(12) United States Patent
Shichitani

(10) Patent No.: US 10,194,665 B2
(45) Date of Patent: Feb. 5, 2019

(54) CLEANING SOLUTION AND MANUFACTURING METHOD THEREFOR

(71) Applicant: Epios Co., LTD, Tokyo (JP)

(72) Inventor: Yasuo Shichitani, Koto-Ku (JP)

(73) Assignee: EPIOS CO., LTD. (JP)

( * ) Notice: Subject to any disclaimer, the term of this patent is extended or adjusted under 35 U.S.C. 154(b) by 0 days.

(21) Appl. No.: 14/915,211

(22) PCT Filed: Aug. 30, 2013

(86) PCT No.: PCT/JP2013/074600
§ 371 (c)(1),
(2) Date: Feb. 26, 2016

(87) PCT Pub. No.: WO2015/029263
PCT Pub. Date: Mar. 5, 2015

(65) Prior Publication Data
US 2016/0205937 A1 Jul. 21, 2016

(51) Int. Cl.
| | |
|---|---|
| C25B 1/26 | (2006.01) |
| A61K 33/20 | (2006.01) |
| A61K 33/14 | (2006.01) |
| A01N 59/00 | (2006.01) |
| A01N 59/08 | (2006.01) |
| C02F 1/467 | (2006.01) |
| A61Q 17/00 | (2006.01) |
| A61Q 19/10 | (2006.01) |
| A61K 8/20 | (2006.01) |
| A61Q 11/00 | (2006.01) |
| C11D 7/08 | (2006.01) |
| C11D 7/10 | (2006.01) |

(52) U.S. Cl.
CPC ............ *A01N 59/00* (2013.01); *A61K 8/20* (2013.01); *A61K 33/20* (2013.01); *A61Q 11/00* (2013.01); *A61Q 17/005* (2013.01); *A61Q 19/10* (2013.01); *C02F 1/4674* (2013.01); *C11D 7/08* (2013.01); *C11D 7/10* (2013.01); *C25B 1/26* (2013.01); *A61K 2800/5922* (2013.01); *A61K 2800/83* (2013.01)

(58) Field of Classification Search
CPC .... A61K 33/20; A61K 33/14; A61K 2800/83; A01N 59/00; A01N 59/08; C25B 1/26; A61L 2/035
See application file for complete search history.

(56) References Cited

U.S. PATENT DOCUMENTS

| | | | |
|---|---|---|---|
| 3,849,281 A | 11/1974 | Bennett et al. | |
| 4,317,709 A | 3/1982 | Ichisaka et al. | |
| 5,674,537 A * | 10/1997 | Morrow | A61K 8/345 424/123 |
| 6,165,343 A * | 12/2000 | Blum | C02F 1/4674 205/556 |
| 2005/0232847 A1* | 10/2005 | Bromberg | A01N 59/00 423/473 |
| 2006/0163085 A1* | 7/2006 | Hanaoka | C02F 1/4618 205/742 |
| 2007/0231247 A1 | 10/2007 | Bromberg et al. | |
| 2010/0285150 A1 | 11/2010 | Noguchi | |
| 2010/0310672 A1* | 12/2010 | Beltrup | C02F 1/4618 424/600 |
| 2011/0135562 A1* | 6/2011 | Niksa | C01B 11/04 423/473 |
| 2011/0159462 A1 | 6/2011 | Asano et al. | |
| 2013/0078196 A1* | 3/2013 | Noguchi | A61K 33/00 424/53 |
| 2015/0044144 A1* | 2/2015 | Lin | A01N 59/00 424/10.3 |

FOREIGN PATENT DOCUMENTS

| | | |
|---|---|---|
| CN | 102217649 A * | 10/2011 |
| JP | S52-28104 B2 | 7/1977 |
| JP | S61-44956 B2 | 10/1986 |
| JP | 5-179475 U | 7/1993 |
| JP | 9-108681 | 4/1997 |
| JP | 2007-530731 A | 11/2007 |
| JP | 2008-260740 A | 10/2008 |
| JP | 2009-029792 A | 2/2009 |
| JP | 4369530 B2 | 11/2009 |
| JP | 2011-132205 A | 7/2011 |
| WO | WO-03/057261 A1 | 7/2003 |
| WO | WO-2011096503 A1 | 8/2011 |

OTHER PUBLICATIONS

Japanese Office Action for JP-2012-033210.
English abstract for JP5-179475.
English abstract for JP-2008-260740.
English abstract for JP-2009-029792.
Japanese Office Action for JP-2012-033210 (cited references JP5-179475, JP-2008-260740, JP-2009-29792 provided above and with English abstracts).

* cited by examiner

Primary Examiner — Tracy Liu
(74) Attorney, Agent, or Firm — Fishman Stewart PLLC

(57) ABSTRACT

The present invention has an object to provide a highly stable cleaning solution that generates a high concentration of hypochlorous acid during cleaning, and has sterilizing and washing out activity on bacteria and viruses. As means for achieving this object, a cleaning solution has been developed which is an aqueous solution containing hypochlorous acid and hypochlorite ions produced using a diaphragm-free electrolysis process. The effective residual chlorine concentration thereof and the hydrogen ion concentration exponent thereof are adjusted to a value from 500 ppm to 2000 ppm and to a value from pH 8.5 to pH 9.5, respectively. Thus, the cleaning solution remains stable for a prolonged period of time, and exhibits high sterilizing and wash-out activity during use.

5 Claims, 4 Drawing Sheets

| CASE OF 0.3% NaCl | | | | | | | |
|---|---|---|---|---|---|---|---|
| ELECTROLYSIS TIME (MIN.) | 0 | 15 | 30 | 45 | 60 | 75 | 90 |
| EFECTIVE CHLORINE (mg/kg) | 0 | 90 | 190 | 320 | 410 | 520 | 590 |
| pH | 7.00 | 9.05 | 9.15 | 9.15 | 9.16 | 9.18 | 9.18 |

| CASE OF 0.8% NaCl | | | | | | |
|---|---|---|---|---|---|---|
| ELECTROLYSIS TIME (HOURS) | 0 | 2 | 4 | 5 | 6 | 7 |
| EFECTIVE CHLORINE (mg/kg) | 0 | 1440 | 2080 | 2328 | 2250 | 2200 |
| pH | 7.20 | 9.30 | 9.35 | 9.35 | 9.38 | 9.35 |

FIG. 5

| pH | 9.0 | MOUTH WASHING TIME 20 SECONDS | 7.0 |
|---|---|---|---|
| Temperature | 18°C | | 36°C |
| HOCL | 12.5ppm | | 71ppm |
| OCL⁻ | 487.5ppm | | 29ppm |

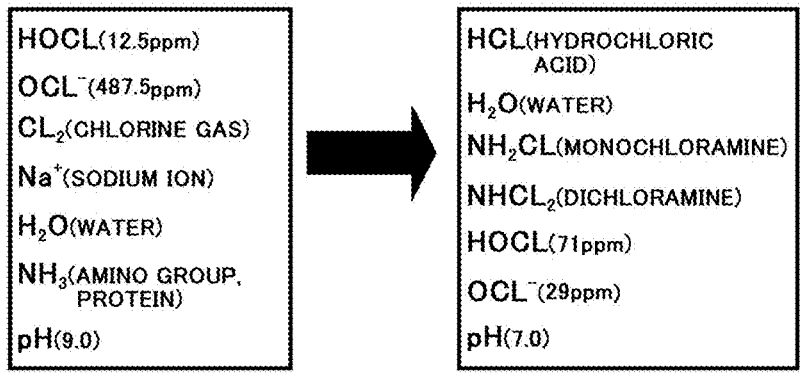

HOCL(12.5ppm)
OCL⁻(487.5ppm)
CL₂(CHLORINE GAS)
Na⁺(SODIUM ION)
H₂O(WATER)
NH₃(AMINO GROUP, PROTEIN)
pH(9.0)

→

HCL(HYDROCHLORIC ACID)
H₂O(WATER)
NH₂CL(MONOCHLORAMINE)
NHCL₂(DICHLORAMINE)
HOCL(71ppm)
OCL⁻(29ppm)
pH(7.0)

FIG. 6

CLEANING SOLUTION AND MANUFACTURING METHOD THEREFOR

CROSS-REFERENCE TO RELATED APPLICATIONS

This application claims priority to PCT Application No. PCT/JP2013/074600, filed Aug. 30, 2013, which is hereby incorporated by reference in its entirety.

TECHNICAL FIELD

The present invention relates to a cleaning solution having protein-removal activity and sterilizing activity.

BACKGROUND

Known, commonly commercially available cleaning solutions that have sterilizing activity include those containing, as the primary component, 1) aqueous hydrogen peroxide solution, 2) sodium chlorite, 3) sodium hypochlorite, and the like. Due to ease of handling or other reasons, those mainly containing sodium hypochlorite are widely used as cleaning solutions that have general sterilizing activity.

Such a cleaning solution is typically produced for use by diluting a high concentration of commercially available stock solution. These cleaning solutions are in widespread use in applications such as disinfectant solutions for hospitals, dental clinics, and the like, and as cleaning solutions for home use, as sterilizing agents, bleaching agents, and oxidizing agents. However, a stock solution adjusted so as to have a high concentration is a strong alkali, meaning that it has a high pH, and is thus hazardous upon contact with the skin etc. In addition, dilution of a stock solution to a suitable pH level causes evolution of chlorine gas and the like, thereby requiring great care. Moreover, problems of toxicity, odor, and other properties thereof always pose problems in storage and management of the chemical solutions.

A sterilizing cleaning process is required in many situations in hospitals and in other facilities, and automatically-controlled conditioning apparatuses for disinfectant solution mainly containing sodium hypochlorite are also available. However, introduction of such large-scale apparatus is limited by cost and floor area, and is thus difficult.

Thus, when a sodium hypochlorite solution generally for sterilization is used as a disinfectant solution, a technique that adjusts the pH, and a technique that uses diaphragm-free or diaphragm-based electrolysis, both after dilution of an aforementioned chemically-synthesized solution, are known (Patent Literature 1).

For producing sodium hypochlorite by electrolysis process, a diaphragm-free and diaphragm-based techniques described above are known. When sodium hypochlorite is produced using a diaphragm, the negative electrode chamber and the positive electrode chamber are separated from each other by the diaphragm, permitting high concentrations of chlorine and alkali hydroxide to react with each other. Accordingly, such method is used in large-scale production of alkali hydroxide and chlorine (Patent Literatures 2, 3, and 4).

However, since the aforementioned method involves handling of a solution containing high concentrations of chemical agents, a dedicated facility is required, which leads to complexity.

Therefore, for production of a sodium hypochlorite solution on a small scale or for home use, a production method by electrolysis of common salt etc. and water using a diaphragm-free process is known. Although the sodium hypochlorite solution produced using the aforementioned method contains a lower concentration of sodium hypochlorite than the concentration of one produced using a diaphragm-based electrolysis technique, bleaching and sterilization can be sufficiently provided. In addition, the method using a diaphragm-free process is advantageous in that production facilities can be provided with a simpler structure.

As also described above, sodium hypochlorite (NaClO) has previously been known as having sterilization efficacy, and it has previously been known that hypochlorous acid (HClO) generated by hydrolysis is the sterilizing component.

It is known that effective chlorine greatly changes its form depending on the pH level. Since it is thought that hypochlorous acid, which provides high sterilization efficacy, rapidly decreases its existing ratio by changing into hypochlorite ions (OCl—) having low sterilizing ability when the pH exceeds 7, and also taking into consideration of preventing evolution of chlorine gas in a strongly acidic pH range, a sterilizing solution is typically adjusted to a value from 3 to 7, in which hypochlorous acid is said to be present in a high existing ratio (Patent Literature 1)

Thus, a generally-used neutral sterilizing solution for dental unit has a pH of from 6.5 to 7.0, and an effective chlorine concentration of from 10 to 40 ppm. A hypochlorous acid solution used for general disinfection or other purpose also has a pH of as low as from 2.2 to 7.5, and an effective chlorine concentration of as low as from 10 to 100 ppm.

However, an affected area in the oral cavity is usually covered with a smear primarily formed of protein. This presents a problem in that, without changing the conditions, application of a sterilizing solution having a predetermined pH concentration that provides sterilizing effects would not allow the sterilizing solution to act directly on the affected area by being blocked by the protein or the like covering the surface of the affected area. Another problem is that even if the sterilizing solution is applied, reaction with a smear (protein etc.) on the affected area and/or with a smear (protein etc.) in a tube of the dental unit prevents sufficient sterilizing ability from being achieved at a predetermined pH that provides sterilizing activity.

SUMMARY

Technical Problem

Thus, the present invention has an object to provide a highly stable cleaning solution capable of exerting sterilizing and washing out actions on bacteria and viruses by generating not only a high concentration of hypochlorous acid but also hypochlorite ions during cleaning, even when a smear formed of protein and the like adheres to a surface to be cleaned.

Solution to Problem

The present invention has been made in view of the foregoing, and is directed to a cleaning solution that is an aqueous solution containing not only hypochlorous acid but also hypochlorite ions under normal storage conditions, which solution is stably present as a sodium hypochlorite solution having an effective residual chlorine concentration of from 500 ppm to 2000 ppm, and having a hydrogen ion concentration exponent of from pH 8.5 to pH 9.5. The cleaning solution is used as a cleaning liquid. As the cleaning solution reacts with a smear, such as protein, that covers an affected area in the oral cavity, and/or with air, protein, etc. present in the dental unit, and provides cleaning efficacy, the pH concentration decreases to a value, for example, in a range of from 5.0 to 7.0, and in turn, the existing ratio of hypochlorous acid in the cleaning solution increases, thereby enhancing the sterilizing ability of the cleaning solution, and thus enabling sterilization of periodontal disease- and dental caries-causing pathogens.

The cleaning solution is a cleaning solution wherein the concentration of NaCl for use in producing the aforementioned cleaning solution is 1% by mass or less, and thus hypochlorous acid can be more efficiently generated by performing a prolonged time of electrolysis on that solution.

The cleaning solution may be a cleaning solution wherein the pH is in a range of from 8.5 to 9.5 upon production, and as cleaning is performed in the oral cavity, the pH decreases to an acidic pH, thereby allowing sterilizing ability by hypochlorous acid to be enhanced.

Advantageous Effects of Invention

According to the present invention, a cleaning solution containing not only hypochlorous acid but also a high concentration of hypochlorite ions can easily be produced in small space, at low cost, and in a safe manner by a diaphragm-free electrolysis process. As a result, a cleaning solution production apparatus can be installed even in, for example, relatively small hospitals, dental clinics, etc. without interfering other devices, thereby permitting mouth rinsing and cleaning of treatment devices to be effectively and continuously performed.

BRIEF DESCRIPTION OF THE DRAWINGS

FIG. 5 is a diagram showing relationships between electrolysis times and effective chlorine concentrations under different concentrations of sodium chloride (NaCl).

FIG. 6 is a diagram illustrating changes in a cleaning solution according to an embodiment of the present invention when mouth washing is performed using the cleaning solution.

DETAILED DESCRIPTION

An embodiment for implementing the present invention will be described below.

Figure 1:
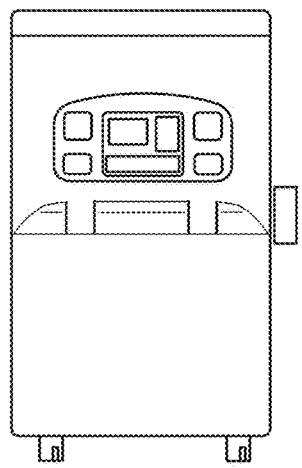
FIG. 1 is an explanatory diagram illustrating the overall appearance of a diaphragm-free electrolyzed water generator.
Figure 2:
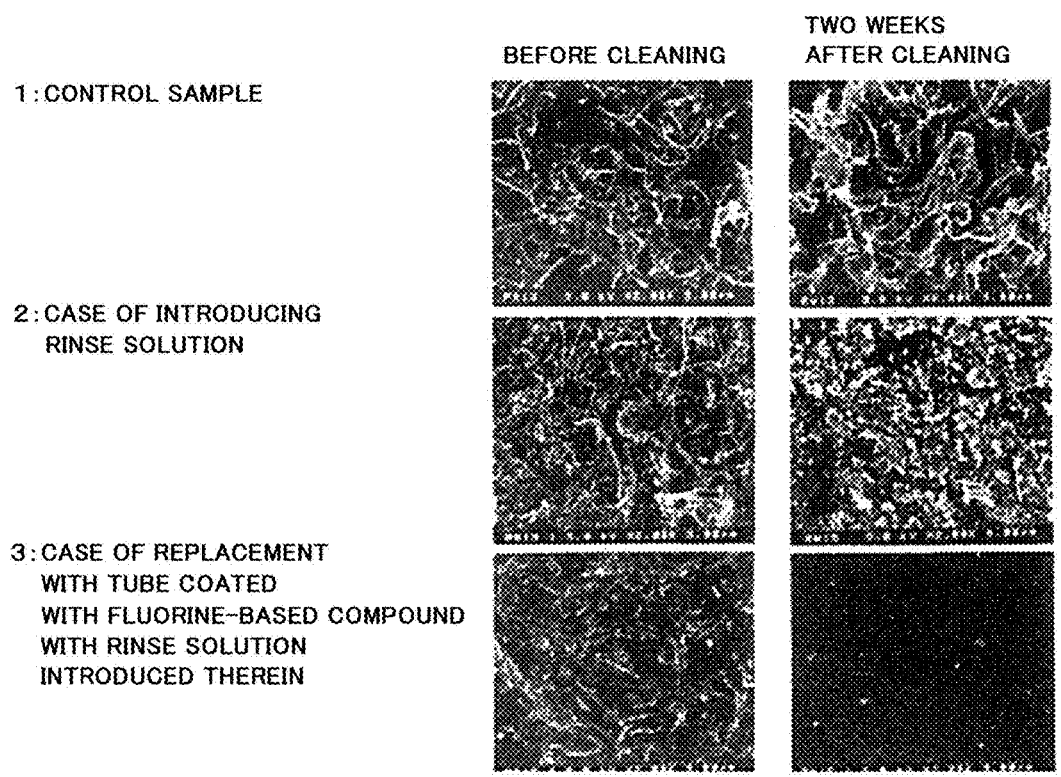
FIG. 2 illustrates a set of photographic images showing wash-out effect on bacteria adhered on an inner surface of a tube of a dental unit.

FIG. 1 illustrates an apparatus for producing a cleaning solution according to this embodiment. As shown in FIG. 1, this cleaning solution is produced by using a diaphragm-free electrolysis process. The apparatus for electrolysis used is a strongly acidic water/strongly alkaline water purifier that uses a cornea-based electrolysis process, manufactured by Aoi Engineering Inc., which was modified such that the diaphragm structure originally provided in the electrolytic cell was removed to arrange a diaphragm-free electrolytic cell, which was used.

The mechanical configuration of the other portions is the same as that for use in the diaphragm-based electrolysis process described above, and uses parts etc. that are typically used in an electrolysis process.

Specifically, the voltage during electrolysis is in a range of from 1 V to 3 V, preferably 2.5 V, and titanium platinum electrodes are used as the electrodes. Next, the electrodes of the negative electrode and the positive electrode are dipped in the aforementioned solution, and a direct current is applied between the two electrodes.

The method of producing the cleaning solution according to this embodiment is to dissolve a small amount (from 0.1% to 2%) of sodium chloride (NaCl) as the electrolyte in ultrapure water having a purity of at least 99% to produce electrolyzed water.

The ultrapure water for use in this embodiment has an electrical resistivity of 15 MΩ·cm or more at a water temperature of 25° C., and a total organic carbon (TOC) of less than 0.05 mg/L.

As a result, ions migrate. This causes water (H2O) to be decomposed, and at the positive electrode, oxygen (O2) gas to be evolved, and the hydrogen (H) ion concentration to be increased.

At the negative electrode, hydrogen (H2) gas is evolved, and the hydroxide (OH) ion concentration increases.

Note that, since this embodiment uses a diaphragm-free electrolysis process, chlorine evolved at the positive electrode reacts with a high concentration of sodium hydroxide generated at the negative electrode to generate sodium hypochlorite.

This process can be expressed as follows:

At negative electrode:

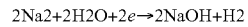

2Na2+2H2O+2e→2NaOH+H2

At positive electrode:

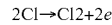

2Cl→Cl2+2e

As a result, it is thought that chlorine and sodium hydroxide react with each other as follows:

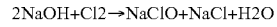

2NaOH+Cl2→NaClO+NaCl+H2O

Experimental examples, examples, and comparative examples will be presented below to describe the present invention in more detail. It is to be appreciated, however, that the present invention is not limited to the examples described below. Note that the component content percentages in the examples all denote percentages by mass.

Example 1

Experiment in Wash-Out Effect on Bacteria Adhered on an Inner Surface of a Tube of a Dental Unit (1) Cleaning Solution The cleaning solution was used which was produced by diaphragm-free electrolysis, and had a pH of from 9.0 to 9.5, and a residual chlorine concentration of from 500 to 600 ppm. Standard tap water was used as the control sample.

(2) Test Method

A comparison was made between the condition of a biofilm on an inner surface of a tube provided for the dental unit before the test, and the condition of the biofilm in the inside of the tube two weeks after the cleaning solution was circulated.

Specifically, a comparison was made between three cases. In case 1, the sample was a control sample; in case 2, the tube was washed with the cleaning solution; and in case 3, a tube coated with fluorine-based compound was washed with the cleaning solution.

(3) Result

Photographic images are shown, each of which shows the condition of bacteria adhered on an inner surface of the tube after the sterilizing solution according to this embodiment was used for washing the inside of a tube of a dental medical device.

As a result, the control sample exhibited formation of a biofilm two weeks after the beginning of the test, subjected to further, recent proliferation.

In contrast, in case 2, where the inside of the tube was washed using the cleaning solution according to this Example, no formation was observed after two weeks elapsed, of a biofilm caused by bacteria such as one recognized at the beginning of the test.

In addition, as shown in case 3, replacement with the aforementioned cleaning solution and with a tube coated with fluorine-based compound resulted in no bacteria found in the tube after two weeks.

As a result, it has been verified that the aforementioned cleaning solution exfoliated the biofilm caused by bacteria formed on an inner surface of the tube, and inhibited further proliferation of bacteria.

Example 2

Characterization Evaluation Experiment on the Cleaning Solution of this Embodiment (1) Cleaning Solution In this Example, a cleaning solution A was used which was produced from the cleaning solution producing apparatus described above, and had a pH of from 9.3 to 9.6, and an effective chlorine concentration of from 500 to 2000 ppm.

(2) Test Method

Mouth washing was carried out using the cleaning solution A, and comparisons were made between pHs and between residual chlorine concentrations both before mouth washing and after mouth washing of 20 seconds. In making a comparison chart, three regions were defined based on the pH and on the effective chlorine concentration, that is, a region of hypochlorous acid water 1 (pH>7.5, effective chlorine concentration: 100 to 2000 ppm), a region of electrolyzed hypochlorite water 2 (pH 7.5 to 9.0), and a region of dilute sodium hypochlorite solution 3 (pH: 2.2 to 7.5, effective chlorine concentration: 10 to 100 ppm). Tap water (pH: 6.0 to 9.0, effective chlorine concentration <1) is also shown for reference purposes.

(3) Result

Figure 3A:
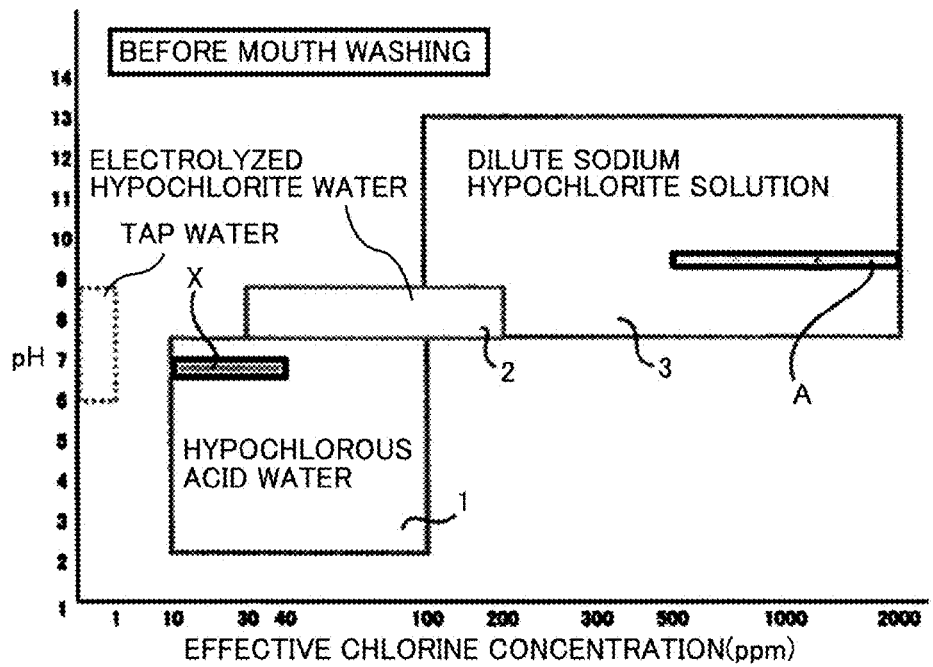
FIGS. 3(a) and 3(b) are each an explanatory diagram illustrating a characteristic test of a cleaning solution.

Next, FIG. 3(a) illustrates and summarizes characteristics of the cleaning solution A used in this embodiment on the region of hypochlorous acid water 1, on the region of electrolyzed hypochlorite water 2, and on the region of dilute sodium hypochlorite solution 3. For reference purposes, a neutral sterilizing agent X for dental unit and tap water are also plotted in the chart described above, based on the respectively corresponding effective chlorine concentration and pH.

Figure 3B:
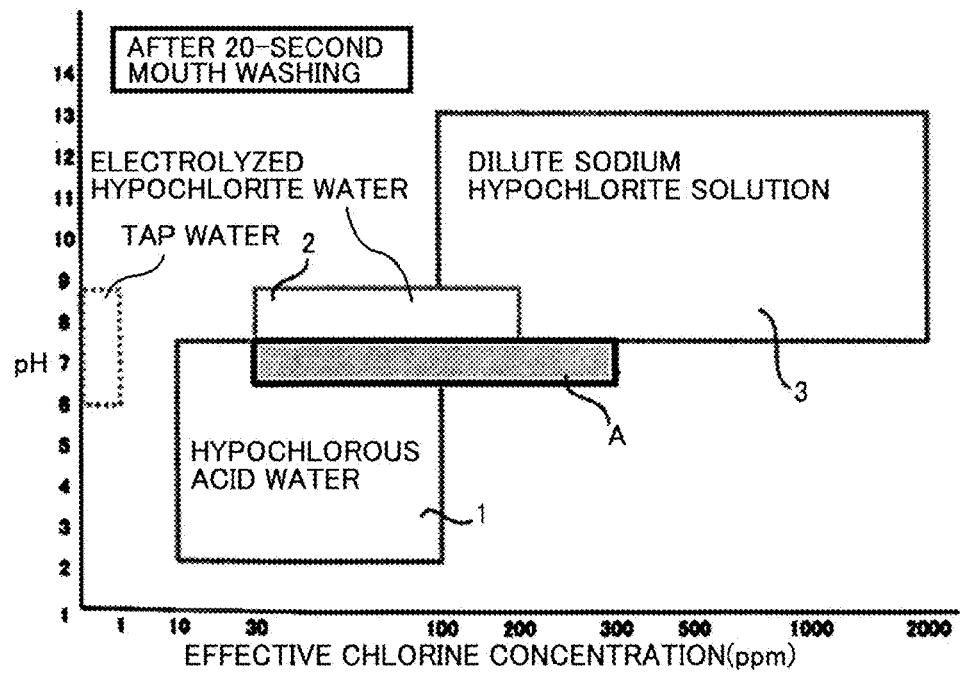

FIG. 3(b) is a chart in which these regions are plotted based on the effective chlorine concentration and pH for the cleaning solution A after mouth washing was carried out for 20 seconds using the cleaning solution A.

This shows that the cleaning solution A before the mouth washing having a relatively high pH of from 9.3 to 9.6 and an effective chlorine concentration of from 500 to 2000 ppm, has changed to a cleaning solution A having a pH of from 6.5 to 7.5 and an effective chlorine concentration of from 30 to 300 ppm.

Figure 4:
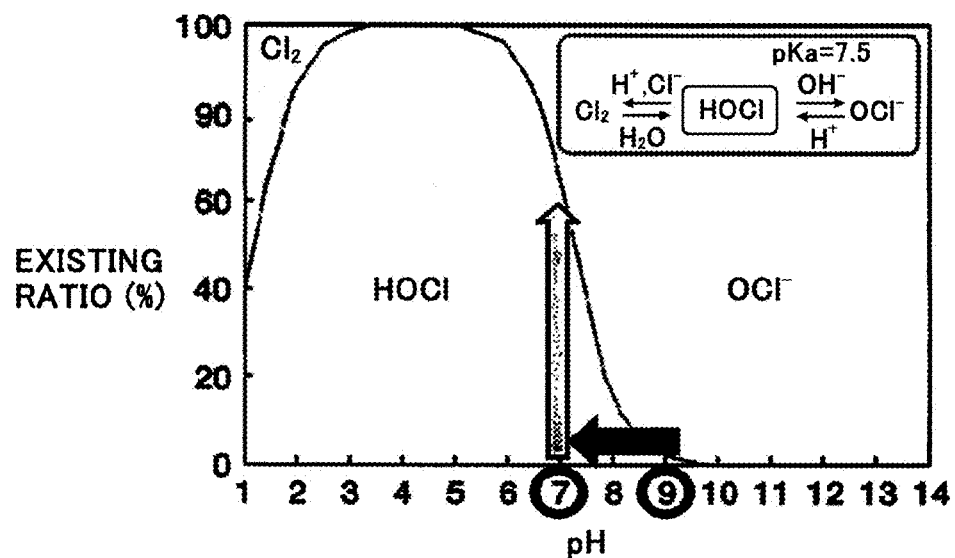
FIG. 4 is an explanatory diagram illustrating a relationship between the existing ratio and pH of hypochlorous acid, and the sterilizing effect thereof.

Now with reference to FIG. 4 illustrating a relationship between the existing ratio and pH of hypochlorous acid, the existing ratio of the hypochlorous acid in the cleaning solution A relates to the change in the existing form dependent on the pH. That is, the existing ratio of hypochlorous acid having high sterilizing ability increases as the pH falls below 9 to an acidic pH. This is thought to be due to the change of the existing form from hypochlorine ions (ClO—) having low sterilizing ability to hypochlorous acid having high sterilizing ability as the pH decreases as shown by the black arrow of FIG. 4.

With this effect, and in consideration of characteristics of the cleaning solution A that inhibits evolution of chlorine gas at a strongly acidic pH, and has high sterilization efficacy, the pH of the cleaning solution A should desirably be adjusted to a pH from 3 to 7, in which the existing ratio of hypochlorous acid is high (FIG. 4).

As shown in FIGS. 3(a), 3(b), and 6, the cleaning solution A before the mouth washing of FIG. 3(a) has a high pH near 9, but after the mouth washing of FIG. 3(b) in the oral cavity, reaction between smears etc. including primarily protein in the oral cavity and the cleaning solution A reduces the pH of the cleaning solution A to pH 7 or less, and in turn, rapidly increases the existing ratio of the hypochlorous acid in the cleaning solution A from 12.5 ppm to 71 ppm. Thus, the cleaning solution A exerts a high sterilizing effect due to hypochlorous acid in oral cavity environment.

Moreover, it is advantageous in that the degree of oxidation is about pH 6 to 7 even after the 20-second mouth washing, and thus there is no concern about chlorine gas evolution.

Example 3

Relationships Between Electrolysis Times and Effective Chlorine Concentrations Under Different Concentrations of Sodium Chloride (NaCl)

(1) Test Method

The diaphragm-free electrolyzed water generator shown in FIG. 1 was used as the test apparatus. This apparatus was charged with electrolyte solution whose sodium chloride (NaCl) concentration had been appropriately adjusted, and an electrolysis process was then started. The pHs and effective chlorine concentrations of the samples were measured at each predetermined elapsed time.

In this Example, tests were carried out for cases where the sodium chloride (NaCl) concentration was 0.3% and 0.8%.

(2) Measurement Method pH measurement: measurement was made using a pH meter (HM-14P of Toa Denpa Kogyo Kabushiki Gaisha) according to pH Determination in General Tests of Japanese Pharmacopoeia.

Effective chlorine: measurement was made using an effective chlorine measurement device (AQUAB AQ-102 of Sibata Scientific Technology Ltd.).

Since the measurement range of effective chlorine concentration of the aforementioned measurement device was 0 to 300 mg/kg, an appropriately-diluted solution was used for measurement.

(3) Result

As shown in FIG. 5, the effective chlorine concentration increased in proportion to the electrolysis time. When the sodium chloride (NaCl) concentration was 0.3%, the effective chlorine concentration exceeded a target value of 500 mg/kg at a time point of 75-minute measurement, when the pH was 9.18. When the sodium chloride (NaCl) concentration was 0.8%, no data were obtained during a time period from 0 minute to two hours (exclusive) after the beginning of the test, but at an elapsed time of two hours, the effective chlorine concentration and pH were 1440 mg/kg and 9.30, respectively. The effective chlorine concentration exceeded the target value for the cleaning solution according to the present invention.

Thus, an intended cleaning solution could be produced by using the apparatus shown in FIG. 1 to perform electrolysis of a solution having a sodium chloride (NaCl) concentration of at least 0.3% for 70 minutes or longer for producing the cleaning solution according to this Example.

When a cleaning solution produced by using the apparatus of FIG. 1 was used in cleaning of a tube of a dental treatment device, and for treatment of periodontal disease and dental caries, based on the test results of Examples 1 to 3 described above, proteolytic action of the aforementioned cleaning solution causes the biofilm adhered in the tube to be peeled off, and prevents bacteria from adhering again, and the inside of the tube can thus be maintained in a sanitary condition. In addition, a case has been reported in which taking advantage of the proteolytic action and sterilizing activity, use of the aforementioned cleaning solution for the purposes of improving the oral cavity environment of periodontal disease patients resulted in significant improvement of the oral cavity environment (not shown). This is thought to be because the sterilizing solution according to the present invention reduced the number of periodontal disease pathogens and of dental caries pathogens in the oral cavity, and degraded and removed protein adhered on surfaces of teeth.

The present invention has an object to provide a highly stable cleaning solution that generates a high concentration of hypochlorous acid during cleaning, and has sterilizing and washing out activity on bacteria and viruses. As means for achieving this object, a cleaning solution has been developed which is an aqueous solution containing hypochlorous acid and hypochlorite ions produced using a diaphragm-free electrolysis process. The effective residual chlorine concentration thereof and the hydrogen ion concentration exponent thereof are adjusted to a value from 500 ppm to 2000 ppm and to a value from pH 8.5 to pH 9.5, respectively. Thus, the cleaning solution remains stable for a prolonged period of time, and exhibits high sterilizing and wash-out activity during use.

The invention claimed is:

1. A method for a cleaning solution, the method comprising:
    providing a cleaning solution of hypochlorous acid and hypochlorite ions that is produced by electrolyzing an electrolyte solution for 70 minutes or longer using a diaphragm-free electrolysis process, the electrolyte solution being prepared by adding, to ultrapure water having a purity of at least 99%, 0.1% by mass to 1% by mass of sodium chloride (NaCl) only, as an additive,
    wherein an effective residual chlorine concentration of the cleaning solution is a value from 500 ppm to 2000 ppm,
    wherein a hydrogen ion concentration exponent of the cleaning solution is a value from pH 9.3 to pH 9.6,
    wherein the cleaning solution is applied during use to a smear that at least includes protein and covers an affected area, and the hypochlorite ions react with and wash out at least part of the smear such that the affected area resists observable biofilm for at least two weeks,
    wherein a decrease of the pH and an increase of a concentration of the hypochlorous acid during use improves a sterilizing effect, and
    wherein the diaphragm-free electrolysis process is at a voltage in a range of 1V to 3V using the electrolyte solution of only the ultrapure water and the sodium chloride.

2. The method according to claim 1,
    wherein the effective residual chlorine concentration of the cleaning solution is decreased to a value from 30 ppm to 300 ppm,
    wherein the pH of the cleaning solution is decreased to a value from pH 6.5 to pH 7.5, and
    wherein the cleaning solution improves the sterilizing effect by way of hypochlorous acid in an oral cavity environment.

3. The method according to claim 1, wherein the cleaning solution is produced without adding a pH adjuster.

4. The method according to claim 1, further comprising:
    applying, while in the electrolyte solution of only the ultrapure water and the sodium chloride, a direct current between negative and positive electrodes including titanium platinum.

5. The method of claim 4, further comprising:
    generating sodium hypochlorite by evolving chlorine at the positive electrode that reacts with a sodium hydroxide generated at the negative electrode.

* * * * *